United States Patent
Biere et al.

(10) Patent No.: US 6,184,351 B1
(45) Date of Patent: Feb. 6, 2001

(54) α-SYNUCLEIN SUPER-MUTANTS ACCELERATE α-SYNUCLEIN AGGREGATION

(75) Inventors: Anja Leona Biere; Martin Citron, both of Thousand Oaks, CA (US)

(73) Assignee: Amgen Inc., Thousand Oaks, CA (US)

( * ) Notice: Under 35 U.S.C. 154(b), the term of this patent shall be extended for 0 days.

(21) Appl. No.: 09/405,035

(22) Filed: Sep. 24, 1999

Related U.S. Application Data

(60) Provisional application No. 60/101,862, filed on Sep. 25, 1998.

(51) Int. Cl.$^7$ .................................................. C07K 14/435
(52) U.S. Cl. ............................. 530/350; 424/9.1; 435/18; 435/71; 435/4; 530/252; 800/8; 514/12; 514/21; 436/501; 436/86; 930/530; 536/23.1
(58) Field of Search .............................. 424/9.1; 435/18, 435/71, 4; 530/350, 252; 800/8; 514/12, 21; 436/501, 86; 930/530

(56) References Cited

PUBLICATIONS

Lewy, F.H., *Handbuch Der Neurologie* "Pathologische Anatomie" (ed. Lewandowski, M.) 920–933, (Springer, Berlin, 1912).

Forno, L.S. *Journal of Neuropathology and Experimental Neurology* "Neuropathology of Parkinson's Disease" vol. 55, 259–272, (1996).

Pollanen, M.S., et al. *Journal of Neuropathology and Experimental Neurology* "Pathology and Biology of the Lewy Body" vol. 52, 183–191, (1993).

Spillantini, G.M., et al. *Proc. Natl. Acad. Science USA* α–Synuclein in filamentous inclusions of Lewy bodies from Parkinson's disease and Dementia with Lewy Bodies: vol. 95, 6469–6473, (May 1998).

Krüger, R., et al. *Nature Genetics* "Ala30Pro mutation in the gene encoding a–synuclein in Parkinson's disease" vol. 18, 106–108, (Feb. 1998).

Polymeropoulos, M. H., et al. *Science* "Mutation in the α–Synuclein Gene Identified in Families with Parkinson's Disease" vol. 276, 2045–2047, (Jun. 1997).

Spillantini, M.G., et al. *Nature* "α–Synuclein in Lewy Bodies" vol. 388, 839–840, (Aug. 1997).

Takeda, A., et al. *American Journal of Pathology* "Abnormal Accumulation of NACP/α–Synuclein in Neurodegenerative Disorders" vol. 152, 367–372, (Feb. 1998).

Baba, M., et al. *American Journal of Pathology* "Aggregation of α–Synuclein in Lewy Bodies of Sporadic Parkinson's Disease and Dementia with Lewy Bodies" vol. 152, 879–884, (Apr. 1998).

Uéda, K., et al. *Proc. Natl. Acad. Science USA* "Molecular cloning of cDNA encoding an unrecognized component of amyloid in Alzheimer disease" vol. 90, 11282–11286, (Dec. 1993).

Weinreb, P.H., et al. *Biochemistry* "NACP, A Protein Implicated in Alzheimer's Disease and Learning, Is Natively Unfolded" vol. 35, 13709–13715, (Oct. 1996).

Jarrett, J.T., et al. *Cell* Seeding "One–dimensional Crystallization of Amyloid: A Pathogenic mechanism in Alzheimer's Disease and Scrapie?" vol. 73, 1055–1058, (Jun. 1993).

Lacey, D.L., et al. *Cell* "Osteoprotegerin Ligand is a Cytokine that Regulates Osteoclast Differentiation and Activation" vol. 93, 165–176, (Apr. 1998).

Dong, A., et al. *Biochemistry* "Secondary Structure of the Pentraxin Female Protein in Water Determined by Infrared Spectroscopy: Effects of Calcium and Phosphorylcholine" vol. 31, 9364–9370, (Jul. 1992).

*Primary Examiner*—Christopher S. F. Low
*Assistant Examiner*—Patricia A. Robinson
(74) *Attorney, Agent, or Firm*—Craig A. Crandall; Ron K. Levy; Steven M. Odre

(57) ABSTRACT

Parkinson's disease (PD) is a neurodegenerative disorder which is pathologically characterized by the presence of intracytoplasmic Lewy bodies, the major component of which are filaments consisting of α-synuclein. The present invention provides α-synuclein mutations which accelerate α-synuclein aggregation and can thus be utilized for transgenic animal production and generation of the first progressive PD model. Also provided is an in vitro aggregation assay which can be utilized to identify α-synuclein nucleation inhibitors for the treatment of PD.

5 Claims, 7 Drawing Sheets

α-SYNUCLEIN SUPER-MUTANTS ACCELERATE α-SYNUCLEIN AGGREGATION

This application claims the benefit of U.S. Provisional Application No. 60/101,862, filed Sep. 25, 1998, which is hereby incorporated by reference.

BACKGROUND OF THE INVENTION

Parkinson's disease (PD) is a progressive, degenerative neurologic disorder which usually occurs in late mid-life, and is the second most common neurodegenerative disorder, after Alzheimer's disease. PD predominantly affects dopaminergic neurons in the nigrastriatal system but also several other regions of the brain, and is clinically characterized by bradykinesia, tremor, and rigidity.

Bradykinesia, a slowness or "poverty" of movement, slows the pace of such ultilitarian activities as walking and eating, and also makes movements that were once second nature take on a ponderous and deliberate quality. Tremor is a shakiness that generally affects limbs that are not otherwise in motion. For those PD patients diagnosed at a relatively young age, tremor is reported as the most disabling symptom. Older patients say their greatest challenge is walking or keeping their balance. Rigidity is caused by the inability of muscles to relax as opposing muscle groups contract, causing tension which can produce aches and pains in the back, neck, shoulders, temples, or chest.

PD is pathologically characterized by nerve cell loss in the substantia nigra and by the presence of intracytoplasmic Lewy bodies. A presynaptic protein, called α-synuclein, has been detected in Lewy bodies and shown to be the major filamentous component in Lewy bodies in PD; Spillantini et al., *Proc. Natl. Acad. Sci.,* 95:6469–6473 (1998).

Synuclein was originally cloned and identified as a synaptic protein in torpedo; Maroteaux et al., *J. Neurosci.,* 8:2804–2815 (1988) and later bovine; Nakjo et al., *Eur. J. Biochem.,* 217:1057–1063 (1993), rat; Maroteaux et al., *Mol. Brain Res.,* 11:335–343 (1991), and human (precursor of the non-Aβ component of Alzheimer's disease amyloid (NACP)); Ueda et al., *Proc. Natl. Aca. Sci. USA,* 90:11282–11286 (1993). Subsequent studies showed that there are two types of synucleins, α and β, and NACP is analogous to α-synuclein; Iwai et al., *Neuron,* 14:467–475 (1994). The function of α-synuclein is unknown, but two naturally occurring mutations in α-synuclein, A53T and A30P, have been linked to familial early-onset PD; Polymeropoulos, et al., *Science,* 276:2045–2047 (1997); Kruger et al., *Nat. Genet.,* 18:106–108 (1998).

Baba et al., *Am. J. Pathol.,* 152:879–884 (1998) reported data strongly implicating α-synuclein in the selective degeneration of neurons in sporadic PD. Baba et al. suggest that the mechanisms leading to the selective incorporation of α-synuclein into Lewy bodies probably involve alterations in the metabolism of α-synuclein that render it insoluble and prone to aggregation. Baba et al. thus postulate that wild type α-synuclein probably plays a role in the pathogenesis of sporadic PD, and that the A53T substitution in α-synuclein may augment the process.

Conway et al., *Nature Medicine,* 4:1318–1320 (1998) then reported that the naturally occurring α-synuclein mutations, A53T and A30P, may promote PD pathogenesis by accelerating α-synuclein fibril formation, which may be an early step in Lewy body formation. Conway et al. utilize an in vitro fibrillization assay; Harper et al., *Ann. Rev. Biochem.,* 66:385–407 (1997), and present data demonstrating that both mutant forms, at high concentrations, form Lewy body-like fibrils and discrete spherical assemblies; most rapidly by the A53T mutant. Based on their findings, Conway et al. postulate that inhibiting α-synuclein fibrillization may be an effective therapeutic strategy against the disease. Conway et al. also state that the in vitro fibrillization assay may allow compound libraries to be screened to identify such α-synuclein fibrillization inhibitors.

Despite these reports and other extensive PD research conducted to date, there is still no known cure for PD. Deprenyl (selegiline), begun early in the disorder, can slow progression of the disease, and there is also evidence that "antioxidants" such as vitamin E and selenium may be of some benefit. There clearly exists the need for improved means of diagnosis and treatment of PD.

SUMMARY OF THE INVENTION

It is therefore an object of the present invention to address this need by providing artificial α-synuclein super-mutants which demonstrate accelerated aggregation as compared to naturally occurring mutants and which can be utilized for transgenic animal production, and subsequent generation of the first progressive PD model.

Also provided is an in vitro aggregation assay which can be used to evaluate α-synuclein super-mutants, and which can be formatted to allow for the high throughput screening for α-synuclein nucleation inhibitors for the treatment of PD.

DETAILED DESCRIPTION OF THE INVENTION

Figure 1:
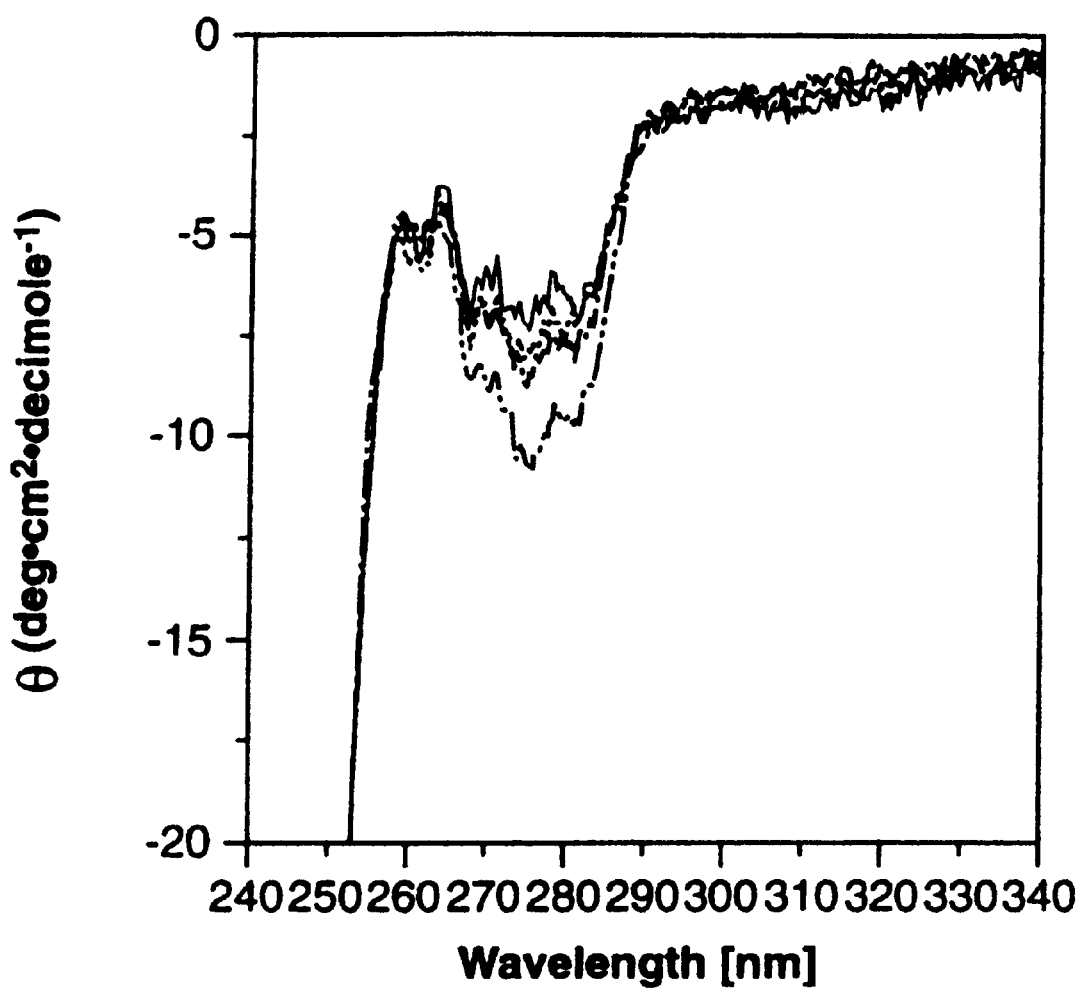
FIG. 1 depicts near UV CD spectra of wild type (--), A30P (. . .), A53T (.-.-.-), and A30P/A53T (..-..-..) α-synuclein in phosphate buffered saline.

The term "isolated polypeptide" refers to a polypeptide of the invention that is free from at least one contaminating polypeptide that is found in its natural environment, and preferably substantially free from any other contaminating mammalian polypeptides which would interfere with its therapeutic or diagnostic use.

To perform the studies of the present invention, human α-synuclein cDNA; Ueda et al., *Proc. Natl. Aca. Sci. USA,* 90:11282–11286 (1993) was cloned, and bacterial expression constructs generated for the wild type protein, the A53T mutant, the A30P mutant, a form containing both the A53T and A30P mutations, and various other mutant forms. The wild type α-synuclein protein sequence used as a template for production of the various mutants of the present invention is that found in SEQ ID NO:1.

To perform the analysis on the various α-synuclein proteins, an in vitro assay was designed to look specifically for instances of accelerated α-synuclein aggregation. The assay generally comprises: concentrating the test sample to 2–7 mg/ml; sterile filtering the sample through 0.22 micron filters to remove any particulate matter; incubating the sample over a specified period of time at 37° C. with defined agitation; centrifuging aliquots of the incubated samples at predetermined times; and analyzing the pellet and supernatant of the aliquoted sample using various conventional techniques.

When the various α-synuclein proteins of the prior art were tested in the assay of the present invention, it was demonstrated that wild type α-synuclein, the naturally occurring A53T mutant form, and the naturally occurring A30P mutant form of α-synuclein can spontaneously form fibrillar β-sheet aggregates. It was also observed that in a complete aggregation time course, α-synuclein aggregation is slow and displays a distinct lag phase. And, importantly, the naturally occurring α-synuclein mutants each showed a reduced lag phase with respect to wild type α-synuclein, and enhanced the aggregation tendency observed in the wild type protein. This is critical, because a pathogenesis model which can cover all known mutants plus the wild type situation is less likely to be based on non disease relevant effects. For example, in the Alzheimer's disease field the key evidence for the amyloid hypothesis is the finding that all known early onset familial Alzheimer's disease mutations have one common effect: they increase Aβ42 production compared to the wild type; Hardy, J., *Trends Neurosci.,* 20:154–159 (1997).

We hypothesized that the accelerated aggregation observed with both naturally occurring α-synuclein mutants was due to an increased tendency to assume the β-sheet conformation found in the aggregates. Thus, other mutations that would cause destabilization of the α-helix and stabilization of β-sheet would be predicted to aggregate faster than the wild type protein, possibly even faster than the naturally occurring mutants. In view of this hypothesis, various other mutants were designed and tested. The first such mutant was a A53T/A30P double mutant, and it was demonstrated that this double mutant aggregated faster than each of the naturally occurring mutants, although the phenomenon was not observed in every instance. We then used several secondary structure prediction algorithms to design other artificial super-mutants; looking specifically for mutations which might further destabilize α-helix and enhance stabilization of β-sheets, and thus further accelerate aggregation in vitro. Standard references which describe algorithms useful for the secondary structure prediction include e.g., Chou and Fasman, *Adv. in Enzymol.,* 47:45–148 (1978) and Garnier et al., *J. Mol. Biol.,* 120:97 (1978).

We believe that very rapidly aggregating mutant α-synuclein is critical for the successful generation of a transgenic model of Lewy body formation, which can then be utilized to see whether such mice develop Parkinsonian symptoms. There have been no reports to date of successful production of a transgenic model using the naturally occurring mutants of the prior art, likely due to the slow aggregation processes associated with those mutants.

Using the secondary structure prediction algorithms, three mutants, E83Q/A90V (SEQ ID NO:2), H50Y/A53T (SEQ ID NO:3), and H50T/A53T/A76T (SEQ ID NO:4), were designed and tested in the in vitro assay. In each instance, the mutants demonstrated enhanced aggregation, with the H50T/A53T/A76T mutant showing the most dramatic effect. Each of these super-mutants were used for transgenic animal production with the goal of generating the first progressive Parkinson's disease model. It is, of course, envisioned that one could design other artificial "super mutants" using these methods.

A transgenic non-human animal comprising a nucleic acid molecule encoding an α-synuclein mutant polypeptide is thus encompassed by the invention. The α-synuclein mutant nucleic acid molecules are introduced into the animal in a manner that allows expression and increased levels of an α-synuclein mutant polypeptide, which may include increased circulating levels. The transgenic non-human animal is preferably a mammal, and more preferably a rodent, such as a rat or a mouse.

Nonhuman transgenic animals that are harboring at least one copy of a transgene comprising a polynucleotide sequence which encodes an α-synuclein super mutant polypeptide operably linked to a transcription regulatory sequence capable of producing expression of the α-synuclein supermutant polypeptide in the transgenic animal will be used as Lewy body disease models. The α-synuclein supermutant polypeptide should be expressed in cells which normally express the naturally occurring endogenous α-synuclein gene.

Additionally, the in vitro system described herein can be readily adapted to high throughput screening for compounds which block α-synuclein nucleation. Such inhibitors could be useful as PD therapeutics if aggregation of α-synuclein is a critical step in all forms of PD.

It is thus contemplated that the assays and mutants of the present invention provide the means to identify potential therapeutics for any disease involving Lewy bodies, e.g., dementia with Lewy bodies, as well as any α-synuclein disorder, including those where α-synuclein is not in form of Lewy bodies, e.g., multiple system atrophy.

EXAMPLE 1

This example describes the cloning and bacterial expression of the wild type α-synuclein protein and various naturally occurring and artificial α-synuclein mutant forms.

A 536 basepair human α-synuclein cDNA was obtained by PCR amplification from an adult human brain cDNA library using primers corresponding to nucleotides 20–42 and 532–556, respectively, of the published sequence; Ueda et al., *Proc. Natl. Aca. Sci. USA,* 90:11282–11286 (1993). PCR based site directed mutagenesis of this sequence was then used to generate the mutant forms A53T, A30P, A53T/A30P, E83Q/A90V, H50Y/A53T, and H50T/A53T/A76T.

For bacterial expression all forms were amplified using the following primers:

TGTGGTCTAGAAGGAGGAATAACATATGGATGTATTCATGAAAG (SEQ ID NO:5)

GTCTGTCAAAGGCCAAGGAGGGTGTTGTG and

GGGACCGCGGCTCGAGATTAGGCTTCAGGTTCGTAGTCTTGATAACCTTCCTCA (SEQ ID NO:6)

to alter 3 codons near the 5' end and 1 codon near the 3' end to more highly utilized *E. coli* codons. The resulting PCR products were digested with NdeI and XhoI and cloned into the *E. coli* expression vector pAMG21; Lacey et al., *Cell*, 93:165–176 (1998). The correct DNA sequence of all constructs was confirmed by DNA sequencing. *E. coli* containing the various plasmids were induced and protein expressed using standard fermentation conditions.

EXAMPLE 2

This example describes the purification and characterization of the various α-synuclein forms prepared in Example 1.

*E. coli* cell paste was homogenized in 20 mM Tris, 100 mM NaCl, pH 7.5, with protease inhibitor cocktail Complete (Boehringer Mannheim). Cells in suspension were broken by passaging through a Microfluidizer and a clarified lysate supernatant was collected after centrifugation at 18,000×g for 45 minutes. *E. coli* contaminating proteins were then acid precipitated by adjusting the pH of the lysate supernatant to pH 3.5 using 10% (v/v) of acetic acid, stirring for 20–30 minutes, and then centrifuging the mixture for 1 hour at 27,000×g. The pH of the resulting supernatant was then adjusted to pH 7.5 using 10% (v/v) of acetic acid, and the sample applied to a Q-Sepharose Fast Flow column (Pharmacia) equilibrated in 20 mM Tris, pH 7.5. The α-synuclein protein was then eluted from the column using a NaCl gradient from 0 to 300 mM NaCl in 20 mM Tris, pH 7.5. The α-synuclein containing fractions were identified by SDS-PAGE and found to be >99% pure. The concentration of α-synuclein was determined by measuring absorbance at 280 nm and employing $$\varepsilon_{280}^{0.1\%}$$

of 0.354, determined by using Genetics Computer Group software.

Figure 2:
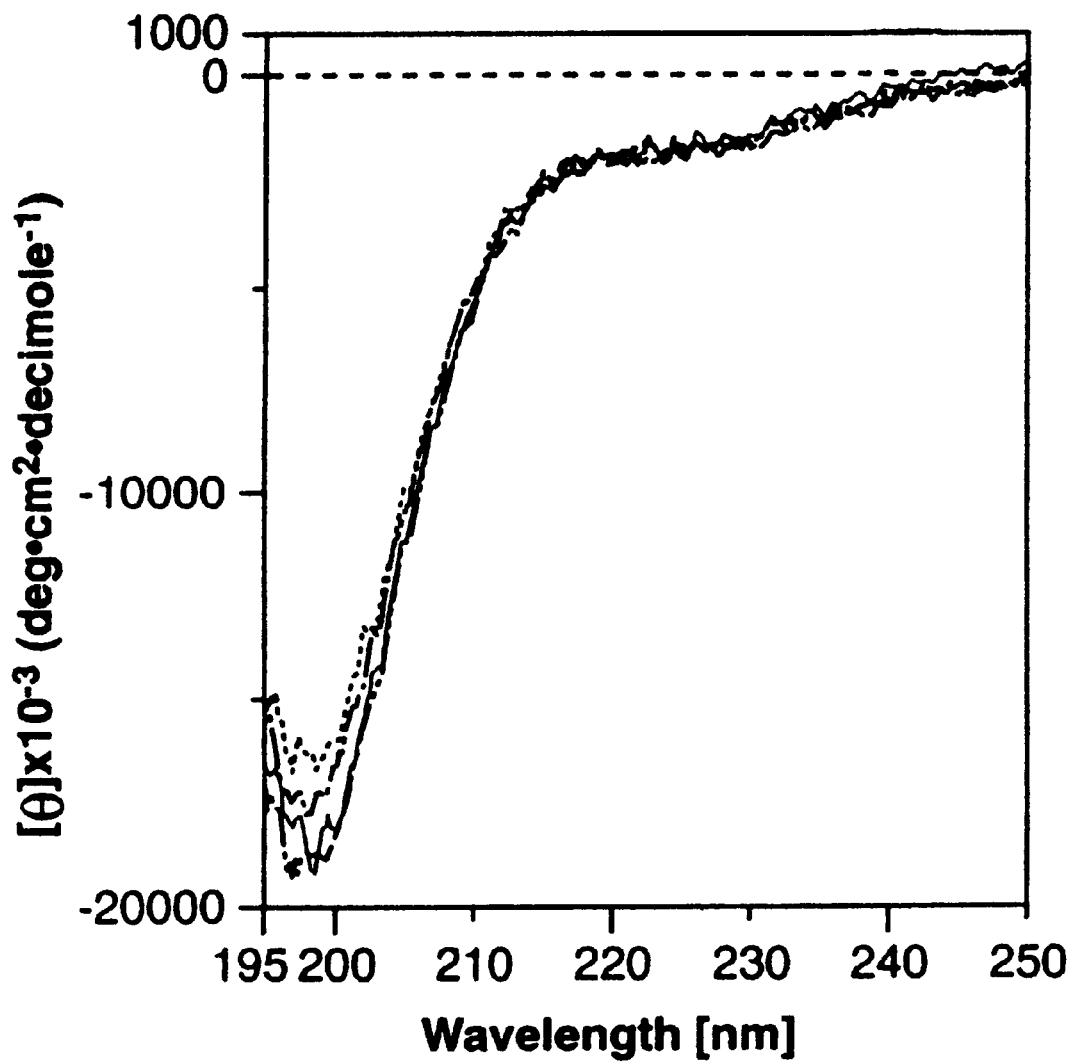
FIG. 2 depicts far UV CD spectra of wild type (--), A30P (. . .), A53T (.-.-.-), and A30P/A53T (..-..-..) α-synuclein in phosphate buffered saline.

To address whether wild type α-synuclein, the naturally occurring A53T α-synuclein mutant, the naturally occurring A30P α-synuclein mutant and an artificial A30P/A53T α-synuclein double mutant differ in their conformation, circular dichroism (CD) and FTIR spectroscopy were performed on the samples. CD spectra were determined at 20° C. on a Jasco J-715 Spectropolarimeter, using water jacketed cuvettes with a pathlength of either 0.01 cm (for the far UV region, 250–190 nm, secondary structure) or 1 cm (for the near UV region, 340–240 nm, tertiary structure). Molar ellipticity was calculated using the protein concentration determined as above, and a Mean Residue Weight of 103. Fresh samples of all proteins showed the natively unfolded structure previously described for the wild type protein; Weinreb et al., *Biochemistry*, 35:13709–13715 (1996), with identical near and far UV CD spectra (see FIGS. 1 and 2).

FTIR spectra of aqueous protein solutions were recorded at 25° C. with a Nicolet Magna 550 Fourier transform infared spectrometer, equipped with a dTGS detector. Protein solutions were prepared for infared measurement in a sample cell (Spectra-Tech FT04-036) that employed $CaF_2$ windows separated by a 6 µm spacer. The final protein spectrum was smoothed with a 7-point Savitsky-Golay smooth function to remove the white noise. Second-derivative spectra were calculated with the derivative function of the Nicolet Omnic software. To quantitate the secondary structure from the second derivative spectra, the spectra were inverted by multiplication by −1 and the curve fit (SpectraCalc Software from Galactic Industries) with Gausian band profiles; Dong et al., *Biochemsitry*, 31:9364–9370 (1992). The FTIR spectra of these molecules were also indistinguishable, and indicated that they contain primarily random coil structure, with the induction of a small amount of helix (about 10%). This data confirms that the initial conformation of the wild type and the mutants is identical.

EXAMPLE 3

This example describes the in vitro aggregation experiments first performed on the wild type α-synuclein, the naturally occurring A53T mutant, the naturally occurring A30P mutant, and the A30P/A53T mutant forms prepared in Example 2.

Purified samples of the four forms were concentrated to >7 mg/ml in Tris-buffered saline (20 mM Tris, 200 mM NaCl, pH 7.5) (TBS)+0.05% sodium azide and then sterile filtered through 0.22 micron filters to remove any particulate matter. Each of the filtrates was then adjusted to a final concentration in the range of ~7 mg/ml in TBS+0.05% sodium azide and incubated over several days at room temperature, 4° C., and 37° C. in parafilm sealed, 1.5 ml ultracentrifuge tubes (Beckman). During the time frame of the experiment, no aggregates formed when incubated at room temperature or at 4° C.

Figure 3:
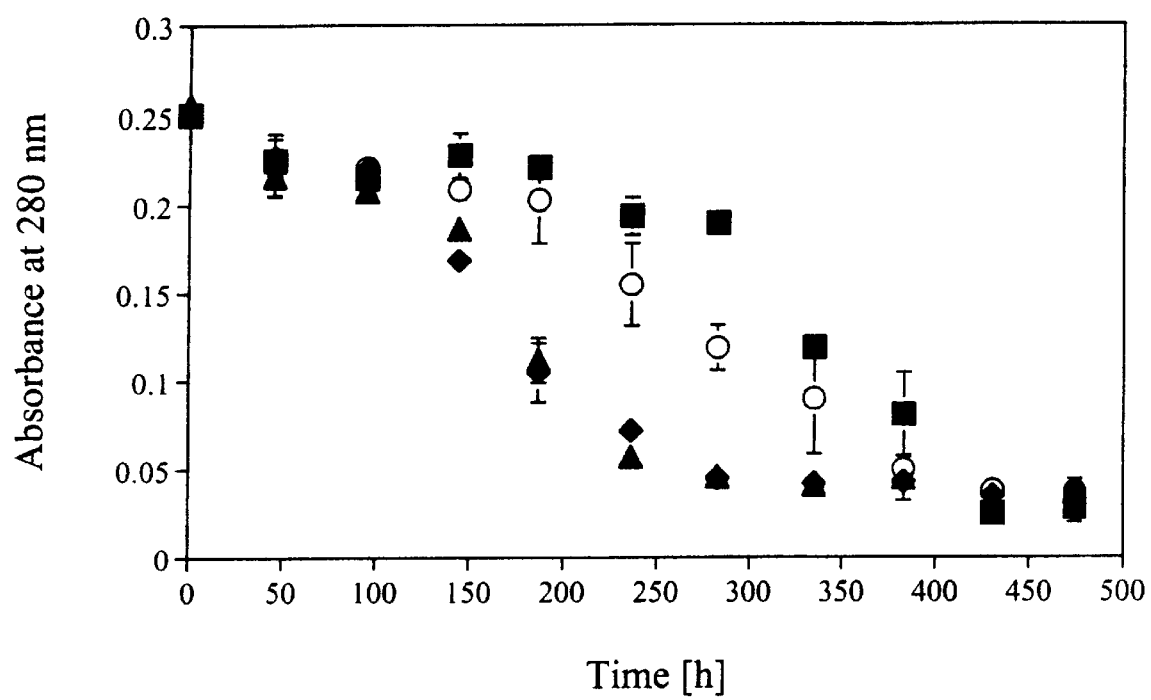
FIG. 3 depicts aggregate formation of wild type (■), A30P (○), A53T (◆), and A30P/A53T (▲) α-synuclein. Aggregate formation was analyzed by measuring the UV absorption at 280 nm of protein in solution after ultracentrifugation. Values are means ±S.E. of three different solutions.

After incubation for several days at 37° C., all samples began to form insoluble aggregates that could be precipitated by ultracentrifugation. The aggregation proceeded until most of the material had fallen out of solution. At various time points, the 37° C. samples were centrifuged at 100,000×g for 10 minutes and the α-synuclein content of the supernatants analyzed by measuring their absorbance at 280 nm. The concentration of α-synuclein was then determined as described in Example 2 (supernatants of samples with concentrations 4 mg/ml or higher were first diluted 1:10 with TBS (11 µl sample+99 µl buffer; supernatants of samples at concentrations below 4 mg/ml were analyzed directly (100 µl)). The nonused portion of all samples were vortexed for 30 seconds to resuspend pelleted material and then allowed to continue incubation at 37° C. If the supernatant was analyzed neat, the 100 µl aliquot used for absorbance measurements was returned to the original incubation tube which was then vortexed for 30 seconds and placed back at 37° C. Curve fits for aggregation time courses (i.e. $A_{280}$ vs. time) were drawn manually (see FIG. 3).

It was observed that in a complete aggregation time course, α-synuclein aggregation is slow and displays a distinct lag phase. The lag phase preceding α-synuclein fibril formation was indicative of a nucleation dependent polymerization and the fact that stirring or shaking dramatically increases the aggregation rate is also supportive of such a mechanism. It was also observed that the aggregate formation was faster for the mutant forms than for the wild type, and the A53T and A30P/A53T mutations had a more dramatic effect than the A30P mutation. The lag time for formation of precipitable aggregates was about 280 hours for the wild type protein, 180 hours for the A30P mutant, and only 100 hours for the A53T and A30P/A53T mutations.

Figure 4:
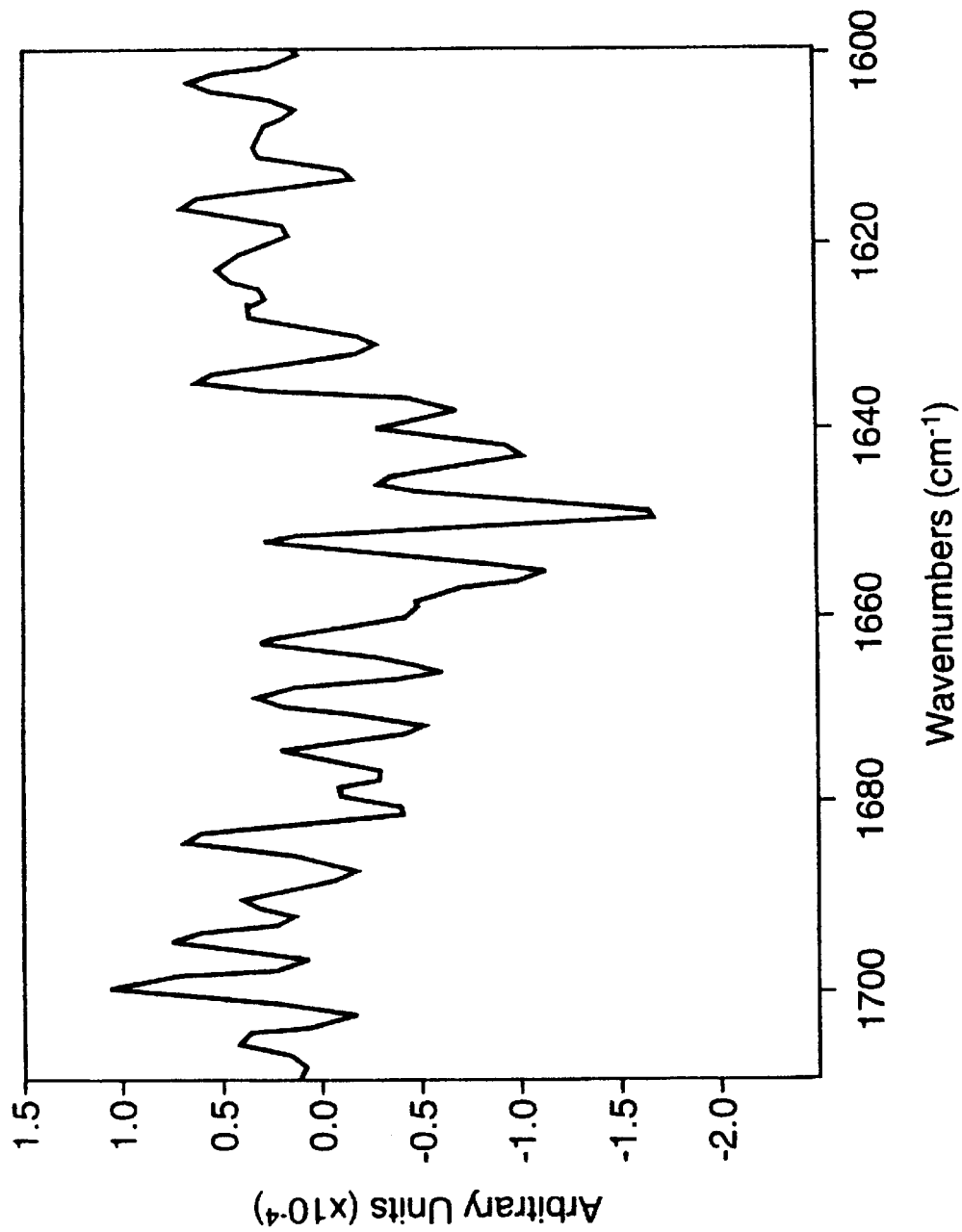
FIG. 4 depicts the second derivative FTIR spectrum of the initial solution of wild type protein. The spectrum shows primary random coil when the α-synuclein is in its solution structure (1650 $cm^{-1}$ band).
Figure 5:
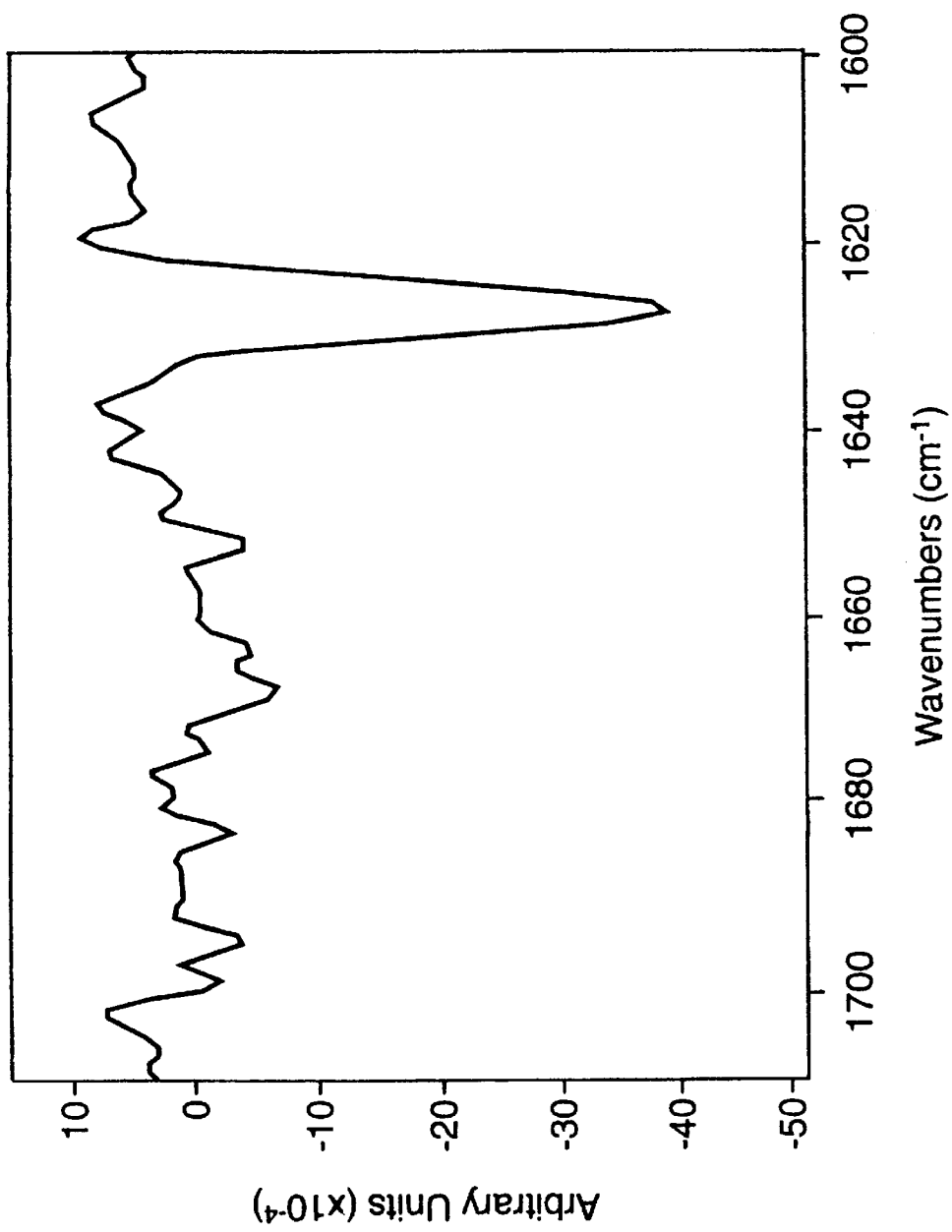
FIG. 5 depicts the second derivative FTIR spectrum of the wild type α-synuclein aggregate. The spectrum shows the final antiparallel β-sheet structure present in the α-synuclein pellet (1629 $cm^{-1}$ band).

At each time point tested, the soluble and insoluble materials were evaluated. The secondary structure of the protein that remained soluble was analyzed by CD and found not to change for any of the proteins throughout the experiments. The structure of the protein that was in the pellet was analyzed by FTIR. Specifically, α-synuclein aggregates were centrifuged at 13,000 rpm for 10 minutes, spread on a 3M disposable IR card, air dried, and the infrared spectra recorded. As FIG. 4 clearly shows, aggregation and precipitation of α-synuclein is accompanied by a dramatic change in secondary structure, from the initial primarily random coil seen when the α-synuclein is in solution structure (1650 cm$^{-1}$ band), to the final antiparallel β-sheet structure present in the α-synuclein pellet (1629 cm$^{-1}$ band, FIG. 5). This structure is commonly observed in protein aggregates. The spectra of the aggregate of all forms are indistinguishable. It was also observed that the loss of soluble material was paralleled by an increase in pellet size.

To address whether the precipitates contain only amorphous aggregates or distinct fibrillar structures, the precipitates were analyzed by electron and atomic force microscopy. Electron Microscopy analysis utilized Formvar coated 300 mesh copper grids which were inverted over 20 μl drops of prepared α-synuclein aggregate suspensions for 10 minutes. The grids were then rinsed in ultrapure water to remove excess, nonadherent material and then allowed to dry at room temperature. The grids were placed sample down on 2% aqueous uranyl acetate for 30 minutes, rinsed in water and allowed to dry. The grids were examined at 120 kV and representative fields photographed at 45,000 diameters magnification on a Philips CM120 transmission electron microscope. Fibrils of the wild type and mutant proteins were readily detected in the precipitates by electron microscopy with positive staining. The diameter of the fibrils is around 12 nm.

Atomic Force Microscopy involved resuspension of the aggregated α-synuclein in PBS and vortexing for 10 seconds. 40 μl of this suspension was incubated on a circular piece of mica for about 3 minutes. Excess liquid was removed and the sample on the mica was then imaged under 40 μl of PBS using a Digital Instruments Nanoscope III atomic force microscope. The probe used for imaging was an oxide-sharpened silicon nitride twin tip with a nominal spring constant of 0.58 N/m. The image was obtained in "tapping mode" in fluid using a drive frequency of 8.67 kHz, a drive amplitude of 200 mV and a setpoint voltage of 0.252 Volts. Fluid phase atomic force microscopy also clearly demonstrated the presence of fibrils in their native aqueous environment.

EXAMPLE 4

This example describes a study wherein the addition of exogenous aggregated α-synuclein functioning as nuclei (seeds) was examined for its ability to start elongation instantly and expedite aggregation.

Solutions of wild type α-synuclein or the A53T mutant at 7 mg/ml were incubated in TBS+0.05% sodium azide at 37° C. for 3 days with continuous shaking (high speed); under these conditions the equilibrium was reached. Critical concentrations were then determined as described by Jarrett et al., *Biochemistry*, 32:4693–4697 (1993) by taking the samples and centrifuging for 10 minutes at 100,000×g, collecting and filtering the supernatant through 0.22 micron filters for analysis by quantitative amino acid analysis to determine protein content.

To perform amino acid analysis, samples were transferred to pyrolized glass vial inserts, dried and then transferred to a Water's Picotag reaction vial, which contained 1 ml of a hydrolysis cocktail (6N hydrochloric acid, 0.05% phenol, 0.001% β-mercaptoethanol). The reaction vial was then purged with nitrogen and then sealed under vacuum; hydrolysis took place at 110° C. for 24 hours. The sample glass inserts were removed and dried, and the samples reconstituted in sample buffer containing the internal standard norleucine. Samples were analyzed on a Beckman 6300 Amino Acid Analyzer (sodium format). Specialized software was used to calculate concentrations from the observed amino acids and internal standard recoveries. The software calculates a correlation coefficient and an average percentage difference between the observed and theoretical number of residues. Reported seed concentrations are based on the amount of monomeric protein used, assuming complete aggregation of the starting material. The material was stored frozen at −20° C. until needed.

Incubations of soluble α-synuclein at concentrations ranging from 2–7 mg/ml in TBS+0.05% sodium azide, were spiked with various amounts of pre-formed α-synuclein aggregates to serve as nuclei for fibril formation. The final concentration of seed is reported as a percentage of the soluble α-synuclein in the incubation (e.g. a 2 mg/ml incubation seeded at a level of 10% contains 0.2 mg/ml seed). Loss of soluble α-synuclein is measured by $A_{280}$ of soluble material following ultracentrifugation as described above.

Figure 6:
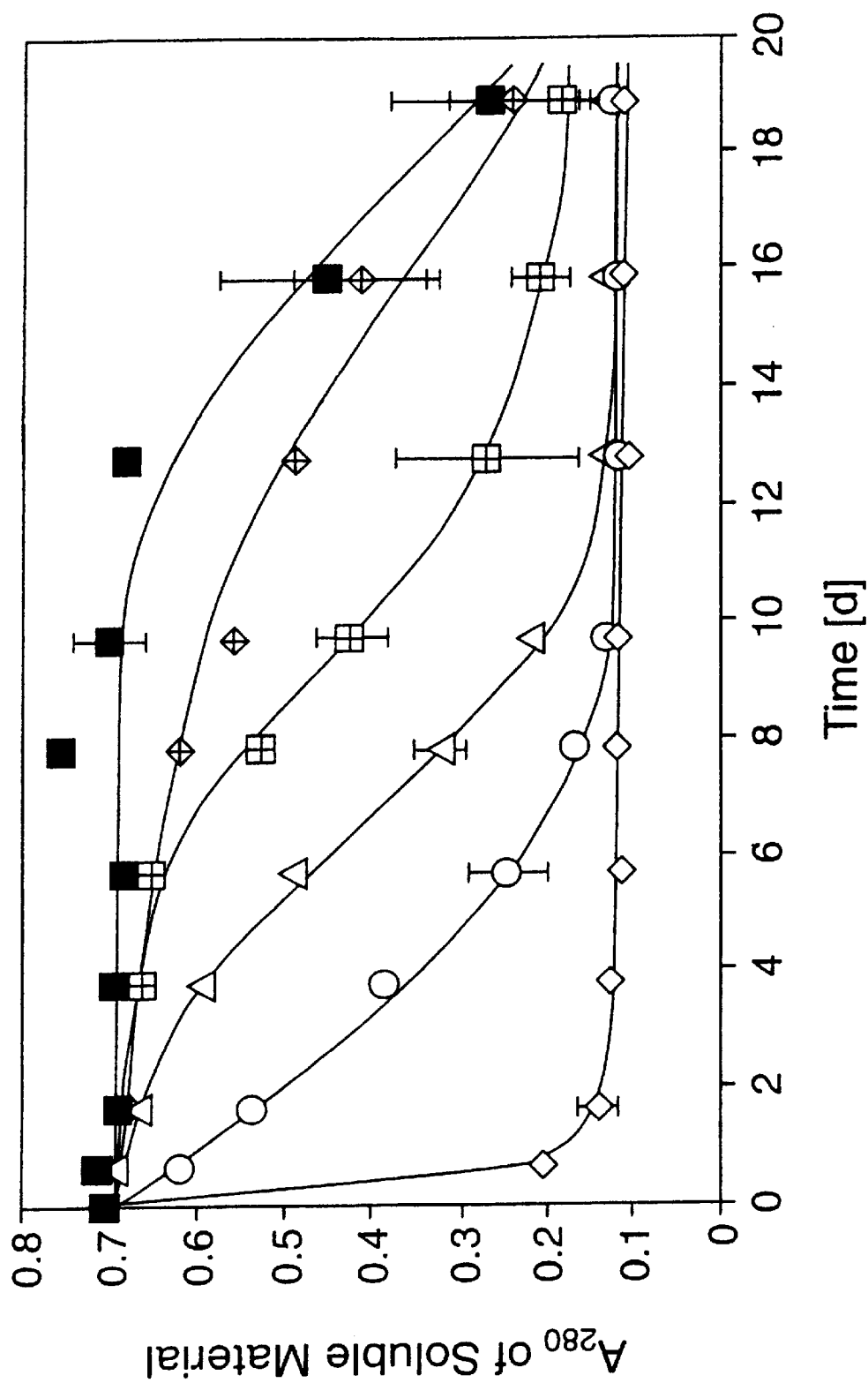
FIG. 6 depicts aggregate formation of wild type α-synuclein at 2 mg/mL as monitored by $A_{280}$ of soluble material following ultracentrifugation. A nonseeded control incubation is shown (■) along with incubations containing preformed wild type α-synuclein aggregate as seed. Seed concentrations, expressed as a percentage of the soluble α-synuclein amount, were 0.001% (◇), 0.01% (⊠), 0.1% (△), 1% (○) and 10% (◇), respectively. Values shown are the average of triplicate incubations ±S.E.

The addition of mutant α-synuclein as seeds to aggregation-competent, supersaturated solutions of wild type α-synuclein bypasses the lag phase and causes rapid aggregation as shown in FIG. 6 (open vs. filled symbols). Seed concentrations in the experiment ranged from 0.001% (◇) of the soluble (α-synuclein amount up to 10% (◇) and it is instantly apparent that the aggregation rate of soluble α-synuclein is controlled by the seed content in a dose dependent manner. Analyzing the data from FIG. 6 as the time required to deplete 50% of the soluble starting material ($t_{1/2}$) allows a quantitative comparison of the seeding efficiency. At 2 mg/ml under our aggregation conditions, unseeded wild type α-synuclein (n) aggregated with a half life of 18 days. With the seed content consisting of only 0.001% (◇) of the soluble α-synuclein, the $t_{1/2}$ already decreased to 16 days. At 0.01% (□) seed the $t_{1/2}$ was 11 days and seed concentrations of 0.1% (Δ), 1% (○) and 10% (◇) seed resulted in a further decrease of half lives to 7, 4 and 0.5 days, respectively.

These studies showed that α-synuclein fibrillogenesis is a nucleation-dependent process that can be seeded by α-synuclein functioning as nuclei. These data lead us to predict that the Lewy bodies of familial PD patients with α-synuclein mutations will contain both the mutant and wild type protein.

It was also determined that the fibril growth follows first-order kinetics with respect to α-synuclein concentration, and wild type and mutant forms of α-synuclein do not differ in their critical concentrations. This data thus confirms that α-synuclein aggregation fulfills all criteria of a nucleation-dependent polymerization process. In this regard, α-synuclein fibril formation resembles that of β-amyloid (Aβ) and paired helical filaments, two protein aggregates characteristic for Alzheimer's disease. And, interestingly, because the critical concentrations of the wild type and mutant α-synuclein do not differ significantly, it suggests that differences in aggregation kinetics of α-synucleins cannot be explained by differences in solubility, but rather are due to different nucleation rates. As such, α-synuclein nucleation appears to be the rate-limiting step for the formation of Lewy body α-synuclein fibrils in PD.

EXAMPLE 5

This example describes the in vitro aggregation experiments performed on the artificial H50Y/A53T mutant, the artificial E83Q/A90V mutant, and the artificial H50T/A53T/A76T mutant. The wild type α-synuclein and naturally occurring A53T mutant served as controls.

Purified samples of the five forms were concentrated to >7 mg/ml in Tris-buffered saline (20 mM Tris, 200 mM NaCl, pH 7.5) (TBS)+0.05% sodium azide and then sterile filtered through 0.22 micron filters to remove any particulate matter. Each of the filtrates was then adjusted to a final concentration in the range of 7 mg/ml in TBS+0.05% sodium azide and incubated over several days at 37° C. in parafilm sealed, 1.5 ml ultracentrifuge tubes (Beckman).

Figure 7:
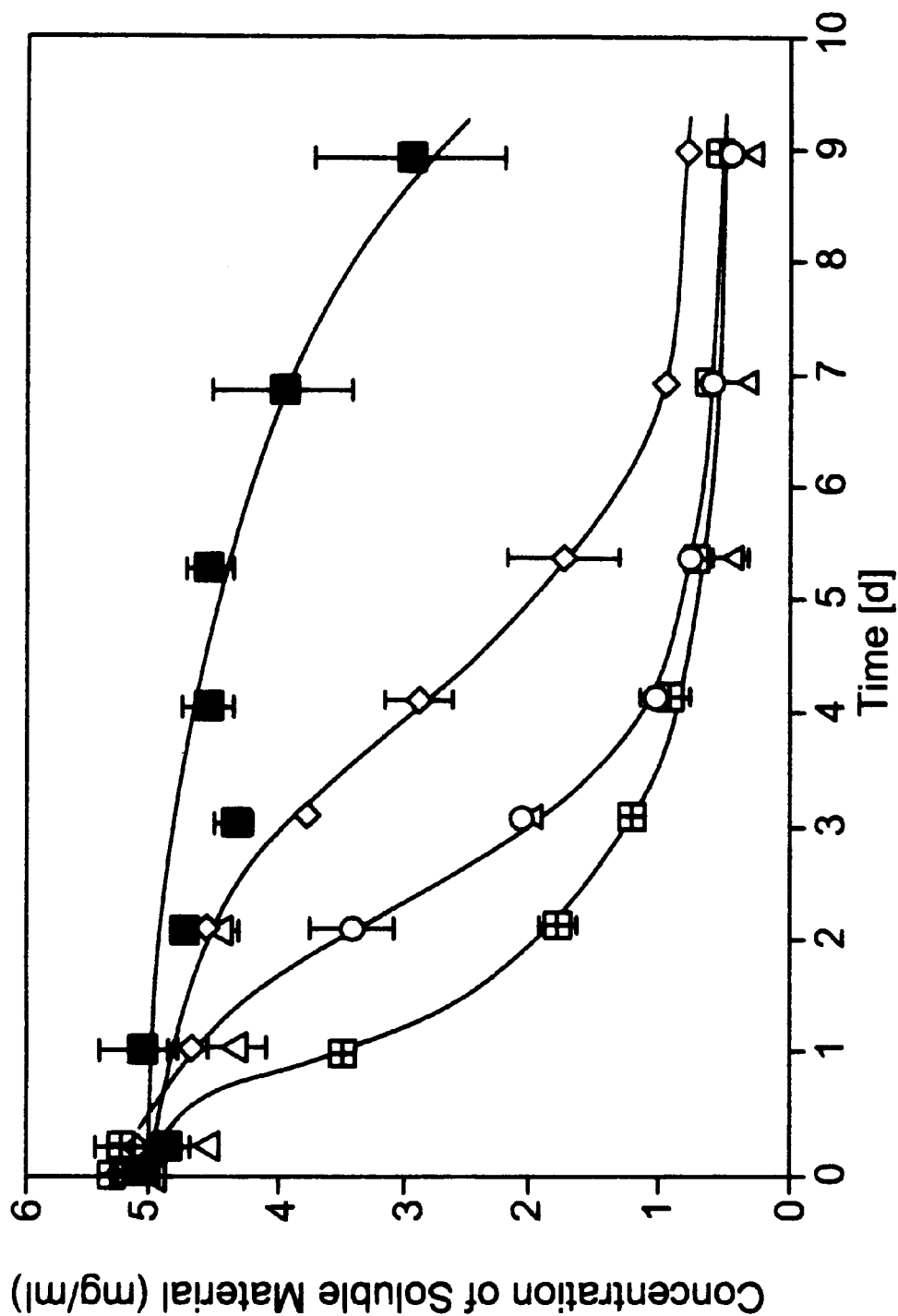
FIG. 7 depicts aggregate formation of wild type (■), A53T (◆), E83Q/A90V (○), H50Y/A53T (△) and H50T/A53T/A76T (□) α-synuclein. Aggregate formation was analyzed by measuring the concentration (mg/mL) of soluble protein in solution after ultracentrifugation. Values are means ±S.E. of three different solutions.

After incubation for several days at 37° C., all samples began to form insoluble aggregates that could be precipitated by ultracentrifugation. The aggregation proceeded until most of the material had fallen out of solution. At various time points, the 37° C. samples were centrifuged at 100,000×g for 10 minutes and the α-synuclein content of the supernatants analyzed by measuring their absorbance at 280 nm. The concentration of α-synuclein was then determined as described in Example 2 (supernatants of samples with concentrations 4 mg/ml or higher were first diluted 1:10 with TBS (11 μl sample+99 μl buffer; supernatants of samples at concentrations below 4 mg/ml were analyzed directly (100 μl)). Curve fits for aggregation time courses (i.e. $A_{280}$ vs. time) were drawn manually (see FIG. 7).

It was observed that the aggregate formation was enhanced for the E83Q/A90V and H50Y/A53T mutants, even when compared to the A53T mutant. And, importantly, the aggregate formation was significantly enhanced for the H50T/A53T/A76T mutant.

EXAMPLE 6

This example describes the use of the E83Q/A90V, H50Y/A53T, and H50T/A53T/A76T forms for transgenic animal production.

For the generation of transgenes, a SmaI fragment of α-synuclein cDNA containing the entire coding region was blunt-end ligated into a blunted XhoI site in exon 2 of the Thy-1 transgene expression vector; Moechars et al., *EMBO JOURNAL.*, 15(6):1265–74, (1996). The transgenic animals were prepared using well known methods such as those described in U.S. Pat. No 5,489,743 and PCT Publication No. WO94/28122, each of which is hereby incorporated by reference in its entirety.

The transgenic animals may be used for drug candidate screening. The impact of a drug candidate on the animal may be measured. For example, drug candidates may decrease expression of the α-synuclein polypeptide gene. In certain embodiments, the amount of α-synuclein polypeptide or a fragment(s) that is produced may be measured after exposure of the animal to the drug candidate. In certain embodiments, one may detect the actual impact of the drug candidate on the animal. For example, overexpression of a particular gene may result in, or be associated with, a disease or pathological condition. In such cases, one may test a drug candidate's ability to decrease expression of the gene or its ability to prevent or inhibit a pathological condition. In other examples, production of a particular metabolic product such as a fragment of a polypeptide, may result in, or be associated with, a disease or pathological condition. In such cases, one may test a drug candidate's ability to decrease production of such a metabolic product or its ability to prevent or inhibit a pathological condition.

The foregoing descriptions of the specific embodiments so fully reveal the general nature and applicability of the present invention that others can readily modify, adapt and/or optimize such specific embodiments for an assortment of assay methods using a variety of reagents and materials, without departing from the present inventive concept. Any such modifications and adaptations are intended to be embraced within the meaning and range of equivalents of this invention.

What is claimed is:

1. An isolated artificial α-synuclein mutant polypeptide which demonstrates accelerated aggregation as compared to naturally occurring α-synuclein mutant polypeptides.

2. A polypeptide of claim 1, said polypeptide comprising the amino acid sequence selected from the group consisting of the amino acid sequence as set forth in at least one of SEQ ID NO:2, SEQ ID NO:3, and SEQ ID NO:4.

3. An in vitro aggregation assay for evaluating α-synuclein mutants which demonstrate accelerated aggregation, said assay comprising the steps of:

(a) generating pure α-synuclein protein;

(b) incubating the α-synuclein solution with defined agitation;
(c) centrifuging aliquots of the incubated samples at predetermined times; and
(4) analyzing the pellet and the supernatant of the aliquoted samples using various conventional techniques.

4. An in vitro aggregation assay for high throughput screening for α-synuclein nucleation inhibitors, said assay comprising:
(a) generating a solution of α-synuclein or aggregation competent fragments of α-synuclein or the mutant polypeptides of claim 1;
(b) incubating said solution with a potential nucleation-affecting agent under conditions that allow α-synuclein aggregation in the absence of the agent;
(c) detecting the amount of aggregated α-synuclein; and
(d) assessing the effect of said agent on the aggregation of α-synuclein.

5. The method of claim 4 wherein the α-synuclein or α-synuclein fragment is labeled radioactively, enzymatically, fluorescently or antigenically.

* * * * *

SEQUENCE LISTING

<160> NUMBER OF SEQ ID NOS: 6

<210> SEQ ID NO 1
<211> LENGTH: 140
<212> TYPE: PRT
<213> ORGANISM: ADULT HUMAN BRAIN

<400> SEQUENCE: 1

Met Asp Val Phe Met Lys Gly Leu Ser Lys Ala Lys Glu Gly Val Val
 1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

-continued

Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                 85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
                115                 120                 125

Ser Glu Glu Gly Tyr Gln Asp Tyr Glu Pro Glu Ala
            130                 135                 140

<210> SEQ ID NO 2
<211> LENGTH: 140
<212> TYPE: PRT
<213> ORGANISM: ADULT HUMAN BRAIN

<400> SEQUENCE: 2

Met Asp Val Phe Met Lys Gly Leu Ser Lys Ala Lys Glu Gly Val Val
  1               5                  10                  15

Ala Ala Ala Glu Lys Thr Lys Gln Gly Val Ala Glu Ala Ala Gly Lys
                 20                  25                  30

Thr Lys Glu Gly Val Leu Tyr Val Gly Ser Lys Thr Lys Glu Gly Val
             35                  40                  45

Val His Gly Val Ala Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Gln Gly Ala Gly Ser Ile Ala Val Ala Thr Gly Phe Val Lys
                 85                  90                  95

Lys Asp Gln Leu Gly Lys Asn Glu Glu Gly Ala Pro Gln Glu Gly Ile
                100                 105                 110

Leu Glu Asp Met Pro Val Asp Pro Asp Asn Glu Ala Tyr Glu Met Pro
                115                 120                 125

Ser Glu Glu Gly Tyr Gln Asp Tyr Glu Pro Glu Ala
            130                 135                 140

<210> SEQ ID NO 3
<211> LENGTH: 140
<212> TYPE: PRT
<213> ORGANISM: ADULT HUMAN BRAIN

<400> SEQUENCE: 3

Met Asp Val Phe Met Lys Gly Leu Ser Lys Ala Lys Glu Gly Val Val
  1               5                  10                  15

Ala Ala Ala Glu Lys Thr Lys Gln Gly Val Ala Glu Ala Ala Gly Lys
                 20                  25                  30

Thr Lys Glu Gly Val Leu Tyr Val Gly Ser Lys Thr Lys Glu Gly Val
             35                  40                  45

Val Tyr Gly Val Thr Thr Val Ala Glu Lys Thr Lys Glu Gln Val Thr
 50                  55                  60

Asn Val Gly Gly Ala Val Val Thr Gly Val Thr Ala Val Ala Gln Lys
 65                  70                  75                  80

Thr Val Glu Gly Ala Gly Ser Ile Ala Ala Ala Thr Gly Phe Val Lys
                 85                  90                  95

Lys Asp Gln Leu Gly Lys Asn Glu Glu Gly Ala Pro Gln Glu Gly Ile
                100                 105                 110

```
Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
        130                 135                 140

<210> SEQ ID NO 4
<211> LENGTH: 140
<212> TYPE: PRT
<213> ORGANISM: ADULT HUMAN BRAIN

<400> SEQUENCE: 4

Met Asp Val Phe Met Lys Gly Leu Ser Lys Ala Lys Glu Gly Val Val
  1               5                  10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val Thr Gly Val Thr Thr Val Ala Glu Lys Thr Lys Glu Gln Val Thr
    50                  55                  60

Asn Val Gly Gly Ala Val Val Thr Gly Val Thr Thr Val Ala Gln Lys
 65                  70                  75                  80

Thr Val Glu Gly Ala Gly Ser Ile Ala Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
        130                 135                 140

<210> SEQ ID NO 5
<211> LENGTH: 73
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
tgtggtctag aaggaggaat aacatatgga tgtattcatg aaaggtctgt caaaggccaa      60
ggagggtgtt gtg                                                        73

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
gggaccgcgg ctcgagatta ggcttcaggt tcgtagtctt gataaccttc ctca           54
```